United States Patent
Catani et al.

(10) Patent No.: US 6,943,248 B2
(45) Date of Patent: Sep. 13, 2005

(54) CRYSTALLINE FORM OF SUCRALOSE, AND METHOD FOR PRODUCING IT

(75) Inventors: Steven J. Catani, Athens, GA (US); Carolyn M. Merkel, North Haledon, NJ (US); Nicholas M. Vernon, Daphne, AL (US)

(73) Assignee: Tate & Lyle Public Limited Company (GB)

( * ) Notice: Subject to any disclaimer, the term of this patent is extended or adjusted under 35 U.S.C. 154(b) by 0 days.

(21) Appl. No.: 10/426,387

(22) Filed: Apr. 30, 2003

(65) Prior Publication Data

US 2004/0220398 A1 Nov. 4, 2004

(51) Int. Cl.⁷ .............................. C07H 1/00; C07H 3/04
(52) U.S. Cl. .................. 536/124; 536/123.13; 536/127; 536/122; 536/4.1
(58) Field of Search ............................ 536/124, 123.13, 536/127, 122, 4.1

(56) References Cited

U.S. PATENT DOCUMENTS

| | | |
|---|---|---|
| 4,343,934 A | 8/1982 | Jenner et al. |
| 4,362,869 A | 12/1982 | Jenner et al. |
| 4,783,526 A | 11/1988 | O'Brien et al. |
| 4,801,700 A | 1/1989 | Tully et al. |
| 4,826,962 A | 5/1989 | Rathbone et al. |
| 4,918,182 A | 4/1990 | Jackson et al. |
| 4,920,207 A | 4/1990 | Sankey et al. |
| 4,950,746 A | 8/1990 | Navia |
| 4,977,254 A | 12/1990 | Homer et al. |
| 4,980,463 A | 12/1990 | Walkup et al. |
| 5,136,031 A | 8/1992 | Khan et al. |
| 5,141,860 A | 8/1992 | Bornemann et al. |
| 5,498,709 A | 3/1996 | Navia et al. |
| 5,530,106 A | 6/1996 | Navia et al. |
| 5,932,720 A | 8/1999 | Sankey |
| 2002/0120134 A1 * | 8/2002 | El Kabbani et al. |

FOREIGN PATENT DOCUMENTS

| | | |
|---|---|---|
| EP | 0 255 260 B1 | 2/1988 |
| EP | 0 708 110 B1 | 4/1996 |
| WO | WO 03/076454 A1 | 9/2003 |

OTHER PUBLICATIONS

TH. Proffen and R.B. Neder; Interactive guide to diffraction, Interactive Tutorial about Diffraction—Powder diffraction: preferred orientation; Mar. 17, 2003; 1 p.; http://www.uni-wuerzburg.de/mineralogie/crystal/teaching/pow_c.html.

David L. Confair and Michael L. Longmire; XRPD Analysis of Sucralose; Nov. 22, 2002; pp. 1–7; a report generated for McNeil Nutritionals by SSCI Inc., West Lafayette, Indiana; Nov. 22, 2002;.

* cited by examiner

Primary Examiner—James O. Wilson
Assistant Examiner—Michael C. Henry
(74) Attorney, Agent, or Firm—RatnerPrestia

(57) ABSTRACT

A crystalline form of sucralose, and a method of making it. The method involves continuously crystallizing sucralose from an aqueous solution by a process providing continuous removal and recirculation of the vessel contents, and providing a long residence time for sucralose in the system. The crystals thus formed are of a relatively low length/diameter ratio, have an unsymmetrical shape, and exhibit good stability. The larger crystals in particular are tapered as compared to the rod-like larger crystals in prior art product.

16 Claims, 5 Drawing Sheets

CRYSTALLINE FORM OF SUCRALOSE, AND METHOD FOR PRODUCING IT

FIELD OF THE INVENTION

This invention relates to stable crystals of sucralose having improved handling properties, and a method for making the crystals.

BACKGROUND OF THE INVENTION

Sucralose, 4,1',6'-trichloro-4,1',6'-trideoxygalactosucrose, a sweetener with a sweetness intensity several hundred times that of sucrose, is made from sucrose by replacing the hydroxyl groups in the 4,1', and 6' positions with chlorine. Synthesis of sucralose is technically challenging because of the need to selectively replace specific hydroxyl groups with chlorine atoms, while preserving other hydroxyl groups including a highly reactive primary hydroxyl group. Numerous approaches to this synthesis have been developed. See, e.g. U.S. Pat. Nos. 4,362,869, 4,826,962, 4,980,463, and 5,141,860, which are expressly incorporated herein by reference.

Crystallization is widely used to purify and recover compounds, including, but not limited to, sugar, sucralose, and related substances. Crystallization is carried out by inducing the formation of crystals in a solution, followed by separating the crystals from the remaining solution (the "mother liquor"), i.e., recovering the crystals.

Sucralose typically crystallizes from water as needle-shaped crystals, as described for example in U.S. Pat. Nos. 4,343,934, 5,136,031, 4,980,463, 4,977,254, 5,530,106, 5,498,709, and 4,950,746. Many of these crystals typically have a length-to-diameter (L/D) ratio ranging from about 4:1 to about 10:1, and in some cases even higher. Indeed, all previously known crystallization processes of which the applicants are aware produce needles of this type. Typically, many such needles are broken, which produces undesirable dust. Nonetheless, at least a significant fraction of the needles remain that have high L/D values. Such crystalline sucralose has poor handling characteristics, including poor flow, which makes it difficult to incorporate into formulations with other ingredients.

Attempts to overcome these difficulties have been reported in the patent literature. For example, U.S. Pat. No. 5,932,720 to Sankey discloses a method for increasing the flowability of crystalline sucralose by treating the crystalline material in a fluidized bed at ambient temperature with additions of water, followed by a fluidized drying phase.

In U.S. Pat. No. 4,918,182 to Jackson et al, there is disclosed crystalline sucralose said to have a mean particle size of at most 10 microns (with 5 microns preferred), the maximum particle size being no more than twice the mean (preferably at most 10 microns). This product is said to exhibit enhanced stability to heat. A method of enhancing the thermal stability of crystalline sucralose is also disclosed, comprising jet milling the sucralose to reduce the particle size, and render the size distribution such that the maximum size is no more than twice the mean.

Notwithstanding the foregoing, there remains a need for stable sucralose crystals that have good flowability characteristics, preferably not requiring post-crystallization processes to modify the crystal shape.

SUMMARY OF THE INVENTION

In one aspect, the invention is a method of producing stable sucralose crystals from a sucralose solution. The method comprises:

introducing a feed stream of sucralose solution into a system;

causing sucralose crystals to form continuously in the system;

removing an output stream of sucralose solution including sucralose crystals from the system; and continuously recirculating a part of the output stream to the system, and separating sucralose crystals from the remaining part of the output stream;

wherein the rates of introducing, removing, and recirculating are controlled so that sucralose passing through the system has, on average, a residence time in the system of at least four hours; and drying the separated sucralose crystals at a drying temperature of about 85° F. or below.

In another aspect, the invention is a composition comprising stable sucralose crystals, at least a portion of the sucralose crystals each comprising a plurality of crystalline sucralose domains.

In still another aspect, the invention is a composition comprising stable sucralose crystals, generally tapered in shape.

DETAILED DESCRIPTION OF THE INVENTION

The invention is described with reference to the figures. Such figures are intended to be illustrative rather than limiting and are included herewith to facilitate the explanation of the present invention. The figures representing process equipment for practicing the invention are not to scale, and are not intended for use as engineering drawings.

Figure 1:
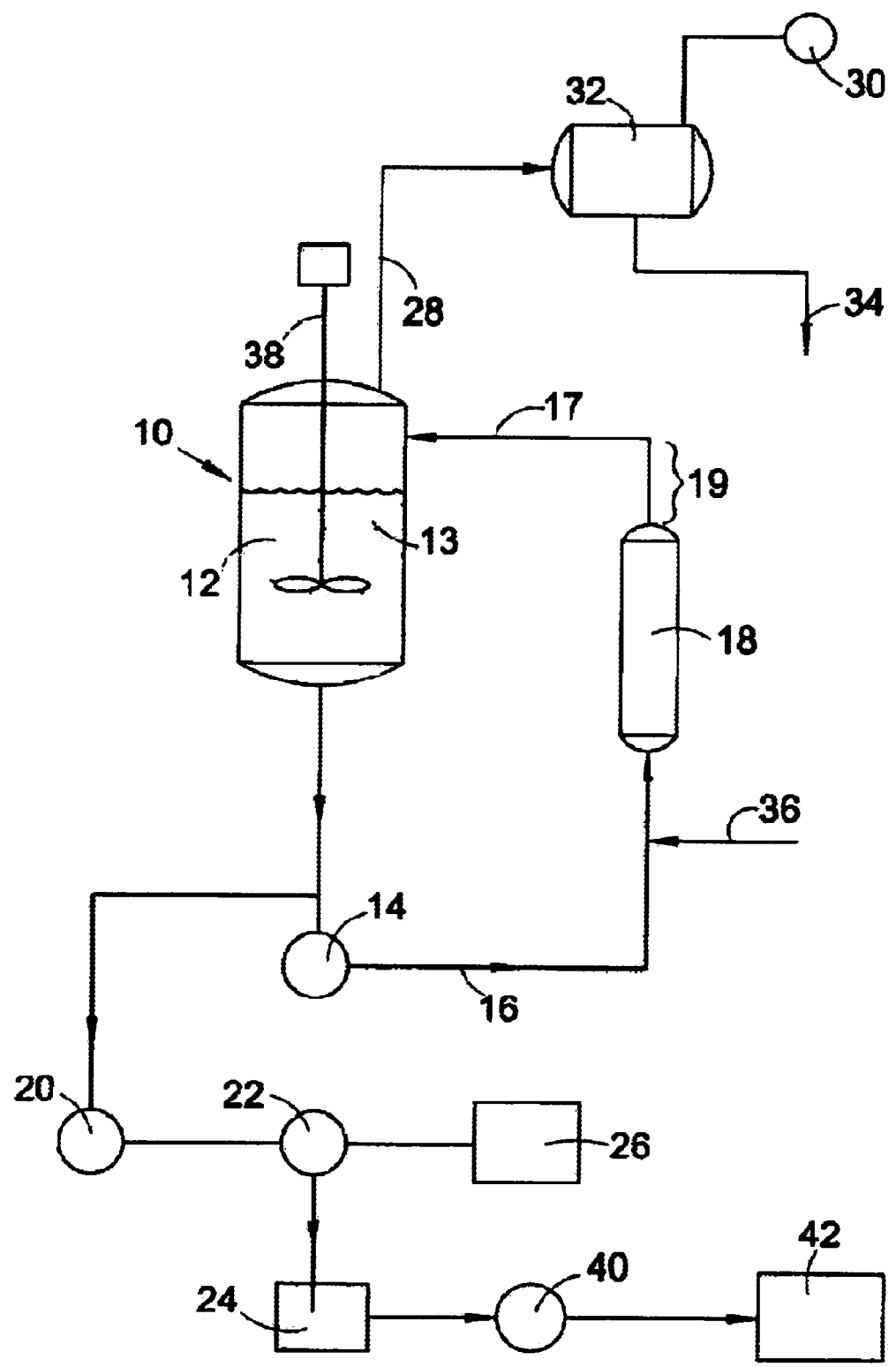
FIG. 1 is a schematic illustration of a crystallizer system suitable for making crystalline sucralose according to the invention.

Referring now to FIG. 1, there is shown in schematic form a crystallization system suitable for preparing stable sucralose crystals, according to one exemplary embodiment of the invention. Crystallizer vessel 10 contains an aqueous solution 12 of sucralose containing suspended sucralose crystals 13. Recirculation pump 14 recycles a portion of the outlet stream from vessel 10 as recirculation stream 16, which passes through and is heated by heat exchanger 18 and empties back into crystallizer vessel 10, thus providing for the presence of circulating sucralose crystals. Although an external heat exchanger is shown in FIG. 1 (heat exchanger 18), other means of heating may be used as well, for example internal heating coils or a heating jacket on vessel 10. A portion of the outlet stream from vessel 10 is drawn off by centrifuge pump 20 and sent to a crystal separator, such as centrifuge 22, which separates moist sucralose crystals 24 from mother liquor 26. This mother liquor is passed on to a separate crystallizer unit (not shown), returned to the vessel 10, discarded, or a combination of these. The moist sucralose crystals 24 are passed through a dryer 40 to provide dried sucralose crystals 42 as the final product, as discussed further below.

As shown in the exemplary embodiment of FIG. 1, water vapor may optionally be drawn from crystallizer vessel 10 by vacuum pump 30 and condensed in condenser 32 to form a liquid water stream 34, which is discarded. By otherwise controlling the temperature of solution 12 in vessel 10, such as by controlling the temperature of recirculation stream 16 using heat exchanger 18 and/or by removing water, the concentration of sucralose is increased to the point of saturation, resulting in the formation of more sucralose crystals. Fresh aqueous sucralose is introduced to the crystallizer vessel as feed stream 36, which in this embodiment is added to recirculation stream 16. An optional agitator assembly 38 may be employed to increase circulation and/or turbulence of sucralose solution 12, to help keep the circulating sucralose crystals 13 suspended and/or to fracture at least a portion of those crystals.

Feed stream 36 may contain from 1% up to the saturation point of sucralose in aqueous solution, with about 20 wt. % being typical. Feed stream 36 may be introduced into the crystallizer system at a temperature of about 100° F. It will be appreciated by those skilled in the art that higher or lower sucralose concentrations and higher or lower temperatures may be used, without departing from the teachings of the invention.

Rates of flow of feed stream 36, in combination with the rate of removal of water 34, moist sucralose crystals 24 and mother liquor 26 from the process, relative to the volume of sucralose solution 12, are typically controlled to give a residence time of sucralose in the crystallizer vessel 10 with a lower limit of about 4 hours, preferably about 6 hours, more preferably about 12 hours. Typically, the residence time will be less than about 100 hours, preferably less than about 50 hours, and more preferably less than about 24 hours.

While feed stream 36 is shown in the embodiment of FIG. 1 as entering the recirculation loop ahead of heat exchanger 18, it may enter the loop after the heat exchanger, or it may enter crystallization vessel 10 directly.

Heat exchanger 18 is typically a tubular heat exchanger, but other types may be used. It is typically controlled to provide a temperature increase of about 2° F. in the recirculation stream 16. Temperature in the crystallizer vessel 10 is typically controlled to be within a range of about 75° F. to about 110° F., and pressure is typically controlled to be from about 0.7 psi (pounds/in$^2$) to 1.2 psi, absolute. It will be appreciated by those skilled in the crystallization art that a variety of combinations of temperature increase in the heat exchanger, vessel temperature, and vessel pressure may be used, with these parameters specified relative to each other by means known in the art to achieve vaporization and removal of water without causing subsurface boiling. Other combinations of temperature and pressure may therefore be used, provided that the temperature does not exceed the melting point of the circulating sucralose crystals 13, and provided that pressure in crystallizer vessel 10 is low enough to afford sufficient vaporization and removal of water. Ultimately, all of these variables are interrelated and controlled to cause the formation of sucralose crystals in vessel 10.

The heated recirculation stream 16 is typically introduced into the head space of the crystallizer vessel 10, where a portion of the water in the combined feed and recirculation stream 17 vaporizes upon entering vessel 10, thereby cooling the liquid and increasing the concentration of sucralose.

Recirculation pump 14 produces a flow rate in recirculation stream 16 sufficient to provide a turnover of the contents of crystallizer vessel 10 in about 2 to about 15 minutes, preferably from about 4 to about 8 minutes. The term "turnover" as used herein refers to a passage through recirculation pump 14 of a volume of liquid equal to the total volume of sucralose solution 12 in the crystallizer vessel 10. Recirculation pump 14 is operated continuously.

As used herein, the unmodified terms "continuous" and "continuously" are to be understood to encompass both fully continuous and intermittent operation, as distinct from a batch operation. Without intending to be bound by any particular explanation or theory, the applicants believe that the continuous turnover provided as described here is important to the formation of sucralose crystals according to the invention.

In the embodiment of the invention depicted in FIG. 1, isolation of the product begins with the discharge of moist sucralose crystals 24 from the centrifuge 22, typically at a moisture level of about 3 wt. %. From the centrifuge the crystals are fed to a screw hopper that holds the crystals while regulating their feed to the dryer. One suitable dryer is a Procedyne Continuous Fluid Bed Dryer, available from Procedyne Corporation of New Brunswick, N.J. Other dryers suitable for use according to the invention are described in U.S. patent application Publication Ser. No. 2002/0120134 A1, published Aug. 29, 2002, incorporated herein by reference. Feed to the dryer goes though a rotary valve that acts as an air lock. Using the Procedyne dryer, air is fed from a distributor at the bottom through the sucralose crystals, thereby fluidizing the bed, and exits the dryer through a ceramic filter. The air is cooled, allowing moisture to condense, recompressed, heated to the specified temperature, and returned to again enter the bottom of the dryer. Nitrogen may be used as the drying medium instead of air. When the fluidized sucralose crystal bed in the dryer reaches a certain level, it overflows through a discharge pipe, and then enters another air lock and is subsequently collected for storage. The moisture content of the dried sucralose crystals 42 may be from about 0.2% to about 10%, typically about 0.5%.

In another exemplary embodiment of the invention, vacuum pump 30 and condenser 32 may be omitted from the embodiment shown in FIG. 1, and crystallization of sucralose may be effected by cooling solution 12 in vessel 10, thereby causing the solubility limit to be exceeded and causing sucralose crystals to form. This cooling may be effected in heat exchanger 18, or some equivalent means of cooling the solution 12. Again, although an external heat exchanger is shown in FIG. 1, other means of cooling may be used as well, for example internal cooling coils or a cooling jacket on vessel 10. By cooling solution 12, the concentration of sucralose is increased to the point of saturation, resulting in the formation of sucralose crystals. In this alternative embodiment, fresh aqueous sucralose is introduced to the crystallizer vessel as feed stream 36, at a temperature higher than that of sucralose solution 12. Preferably, the feed stream 36 is nearly saturated with sucralose, so that a good yield of sucralose crystals can be obtained. As in the first embodiment, an optional agitator assembly 38 may be employed to increase circulation and/or turbulence of sucralose solution 12.

In this embodiment, feed stream 36, typically containing about 50 wt. % sucralose in water, is introduced into the crystallizer system at a temperature of about 200° F. Heat exchanger 18, typically a tubular heat exchanger, is controlled to provide a temperature decrease of about 2° F. in the recirculation stream 16. Temperature in the crystallizer vessel 10 is controlled to be within a range of about 75° F.

to about 110° F. Feed stream 36 may be fed fully continuously into the system, or the feed may be intermittent.

Still other embodiments may comprise some combination of the two embodiments described above.

It has been found that the shelf life of the dried sucralose crystals 42 of this invention is higher but has a somewhat higher sensitivity to drying conditions than do prior art crystals, and a greater sensitivity to the amount of moisture retained in them. Shelf life of crystalline sucralose is commonly estimated by performing an accelerated aging test. In this test the crystals are maintained in a controlled atmosphere at 50° C. (122° F.), and sampled periodically. Each sample is dissolved in water and the pH of a 10% solution is tracked to determine the elapsed time at which the pH drops by one unit, indicating a slight sucralose decomposition. Crystals made by traditional methods are considered stable when such decomposition is not indicated until at least 3 days in this test. This is considered equivalent to a shelf life under ambient conditions of about 8 years.

To obtain stable crystalline sucralose in accordance with the present invention, i.e. crystalline sucralose meeting the above shelf life test, it is important to limit the temperature at which the crystalline product is dried to about 85° F. or less. A drying temperature in the range of about 50° F. to about 70° F. is preferred, with a temperature of about 60° F. being typical. In addition, as disclosed in U.S. patent application Publication Ser. No. 2002/0120134 A1, moisture content of the crystalline product has a substantial effect on stability, with higher levels tending to improve stability. A moisture level between about 0.2 wt. % and about 10 wt. % is suitable, with 0.5 wt. % preferred, in order to provide stable crystalline product according to this invention. When dried at the preferred temperature and to moisture levels typical of old crystals showing the noted pH drop under accelerated conditions in 3 days, the new crystal do not show a drop for at least 3, more typical 4–6, and often more than 6 days.

Shelf life or stability of the dried crystals 42 may also be improved by controlling the pH of the sucralose solution 12 in the crystallizer. To this end, it is also helpful to buffer the sucralose solution 12 to a pH of from about 5.5 to about 8.5, preferably about 6.5 to about 7.8, and more preferably about 7 to 7.8. An exemplary buffer comprises sodium acetate, but others may be used.

Figure 2:
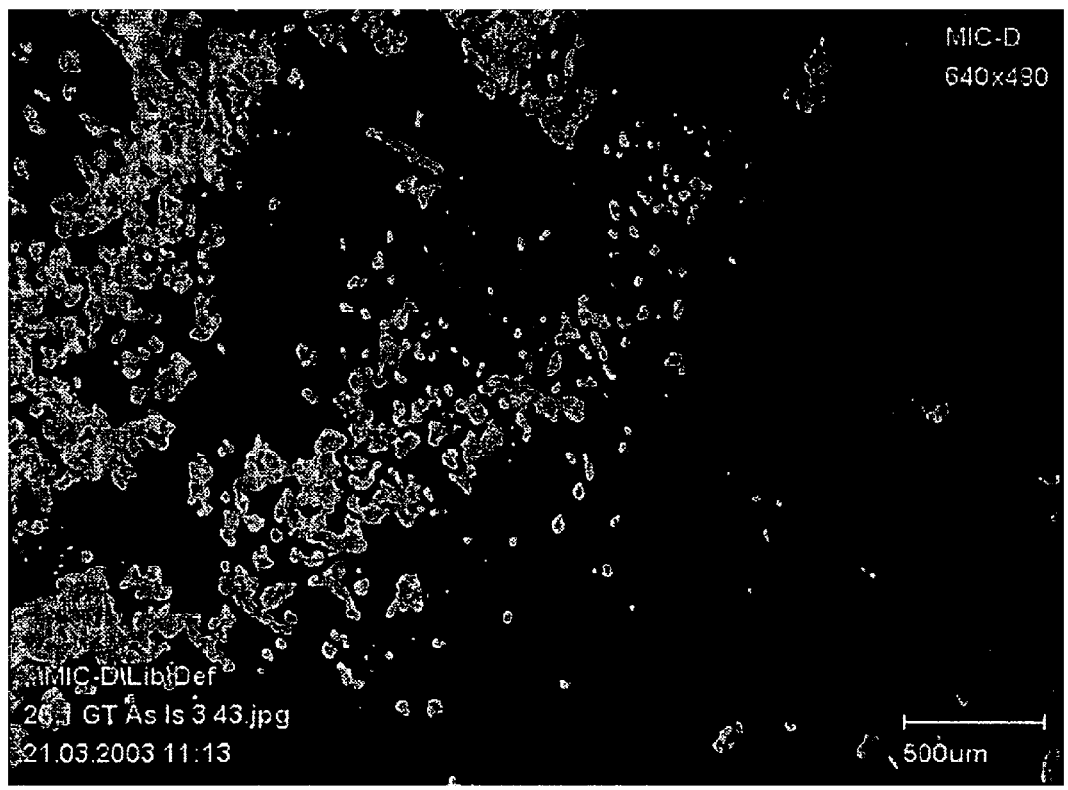
FIG. 2 is a photomicrograph of prior art sucralose crystals.
Figure 3:
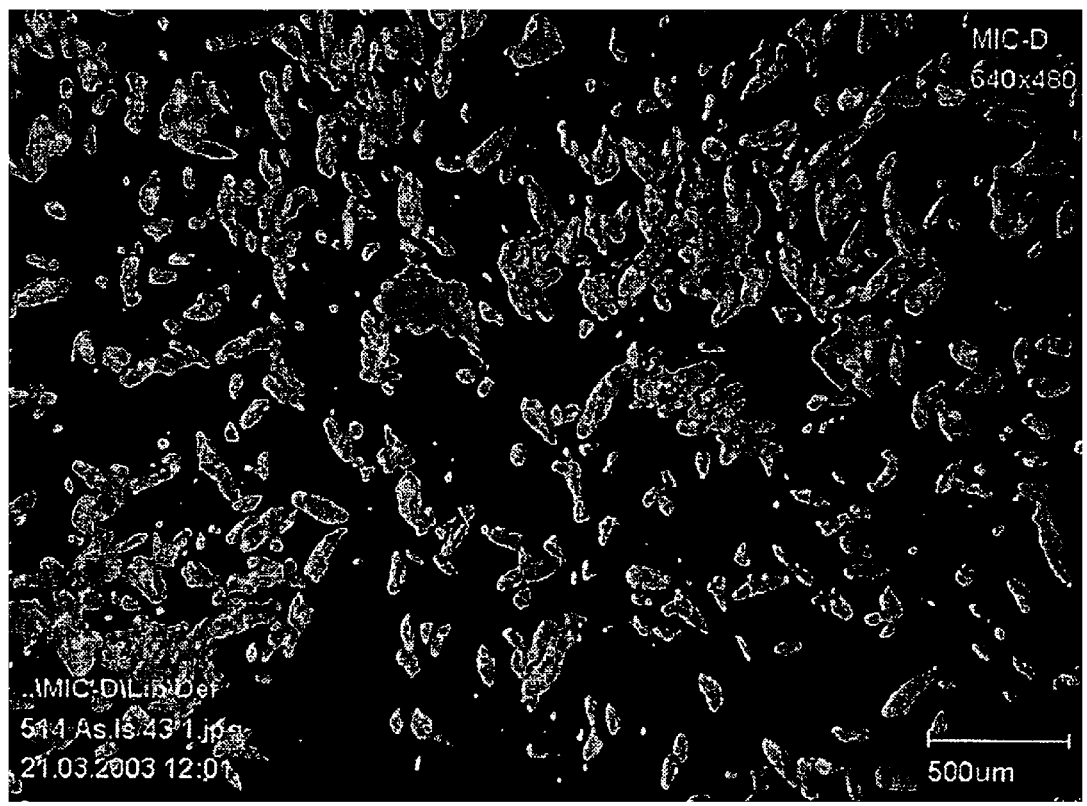
FIG. 3 is a photomicrograph of sucralose crystals according to the invention.

Attention is now drawn to FIGS. 2–5, which are photomicrographs of prior art sucralose crystals and crystals made according to the invention. FIG. 2 shows an unfractionated sample of typical prior art sucralose crystals, and FIG. 3 shows an unfractionated sample of typical product made in accordance with the present invention.

Figure 4:
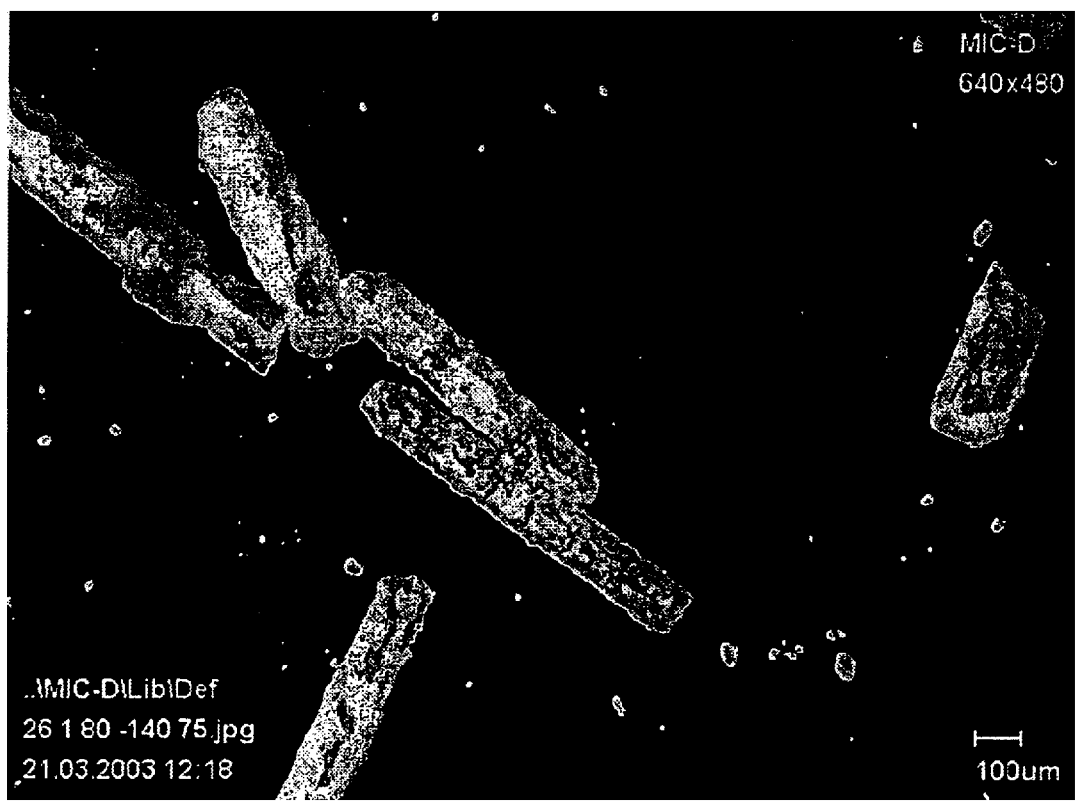
FIG. 4 is a photomicrograph of a sieved fraction of prior art sucralose crystals.
Figure 5:
FIG. 5 is a photomicrograph of a sieved fraction of sucralose crystals according to the invention.

FIG. 4 shows material from a typical prior art sample of sucralose crystals that passed through an 80-mesh sieve but was retained on a 140-mesh sieve. FIG. 5 shows material from a typical sample of sucralose crystals according to the invention that passed through an 80-mesh sieve but was retained on a 140-mesh sieve. Thus FIGS. 4 and 5 allow a clearer view of the larger size fraction of crystals present in the prior art and inventive sucralose products, respectively.

As seen in FIG. 3, sucralose crystals of this invention generally have a somewhat elongated, unsymmetrical appearance. Crystals representing a full (unfractionated) sample typically have a particle size distribution such that 90 wt. % of the sample has a particle size less than from about 30 $\mu$m to about 150 $\mu$m, more typically from about 40 $\mu$m to about 100 $\mu$m, while 10 wt. % has a particle size less than from about 3 $\mu$m to about 40 $\mu$m, more typically from about 4 $\mu$m to about 9 $\mu$m. Sucralose crystals made according to the invention also generally have, on average for a given sample, a length to diameter (L/D) ratio of less than about 6, and preferably less than about 4. As used herein, the crystal length is taken as the length of the longest dimension of the crystal, and the width is the greatest width measurable at right angles to the longest dimension.

As can be seen in comparing FIGS. 4 and 5, the larger particle size fraction of sucralose crystals made according to the present invention comprises crystals having a shape that differs from the long, thin, substantially symmetrical needles that normally comprise the larger particle size fraction of prior art sucralose. Rather, crystals in the larger size fraction of the present invention are characterized in general by the absence of parallel surfaces on substantially all crystals, and tend instead to be characterized by tapered or rounded tapered segments, for example. Many of the crystals comprise a single tapered segment, and most of the crystals are irregularly shaped with no clear symmetry.

Without intending to be bound by any particular theory or explanation, the applicants believe that the sucralose crystals of this invention owe their unusual and beneficial shape and properties to the continuous recirculation of the crystals through the crystallizer system, and to the control of input and output rates to give a relatively long residence time of sucralose in the system. Under these conditions, it is believed that the sucralose crystals are subjected to sufficient mechanical disturbance that at least a portion of the crystals, especially long thin ones such as might be initially formed, are fractured. The fracturing may occur in the recirculation pump 14, in the heat exchanger 18, in bends in the piping of the system, by crystal-crystal contact, and/or by other means.

Such fracturing of crystals may at least partially account for the relatively low L/D ratio of crystals formed according to the invention. In addition, it is believed that, under these conditions, new sites for crystal growth are generated on existing crystals, and that subsequent deposition of sucralose from solution onto these sites results in the formation of the unsymmetrical and irregularly shaped crystals of this invention. Perhaps in addition to this crystal growth on new sites, or instead of it, it may be that, given the relatively long residence time of sucralose in the system, agglomeration of smaller crystals forms the irregular shapes that are typically seen in sucralose crystals according to the invention. It is further believed that, due to such crystal growth and/or agglomeration, many of the crystals of this invention comprise a plurality of crystalline sucralose domains.

Sucralose crystals according to the invention have excellent handling properties and flowability. One measure of these characteristics is the angle of repose, defined as the steepest angle (relative to the horizontal) that can be maintained on a pile of the crystals. A low angle of repose indicates a powder that flows well, a desirable characteristic for handling, as well as for ease of mixing with other ingredients in formulations containing sucralose. Sucralose crystals according to the invention generally have an angle of repose less than about 42 degrees. Sucralose crystals made according to prior art crystallization methods typically exhibit somewhat higher angles of repose.

Another advantageous property of the sucralose crystals of this invention is that, since no mechanical diminution process is performed on the isolated crystals (as is the case with some prior art processes), the product is relatively free of dust.

EXAMPLE

A system as seen in FIG. 1 comprises a vertical cylindrical tank as the crystallizer vessel, with a 4-foot diameter, a 12-foot straight side, a 45-degree cone bottom, and an 8-inch bottom discharge nozzle.

Crystallizer recirculation pump 14 comprises a Model MPAF axial flow centrifugal pump, in which the inlet, outlet, and impeller are all ten inches in diameter (source: Goulds Pumps of Seneca Falls, N.Y.). The pump is operated fully continuously (i.e. not intermittently) at a rate sufficient to provide a turnover of the vessel contents about every 5 minutes.

The entry point of the recirculation stream into the crystallizer vessel is configured to provide a tangential entry of the liquid, resulting in a turbulent or swirling motion that assists in keeping circulating sucralose crystals suspended in the vessel contents. The system is provided with a TEMA class BEM shell-and-tube single pass heat exchanger 18. Such heat exchangers are widely available from a number of manufacturers, and are well known in the industry. The heat exchanger has a 0.5-in to 1.5-in tube size, and is positioned relative to the crystallizer vessel 10 such that a static liquid head of 2–5 feet is maintained over the exchanger, thereby preventing premature flashing of water vapor from the heated recirculation stream before entering the headspace of the vessel. Typically, boiling of the liquid in the system is minimized in order to avoid uncontrolled nucleation of sucralose crystals, as well as the formation of encrustations of sucralose crystals on the inner surfaces of the crystallizer.

Centrifuge 22 is a model HZ 1250 Ph (Pharmaceutical) Horizontal Peeler centrifuge, available from Krauss-Maffei Process Technology Inc. of Florence, Ky. The unit is equipped with an assisted discharge unit, and has a 49.2" diameter×25.125" deep opening, housing a 1-piece seamless polyester screen with built-in coarse backing. The dryer is a Procedyne Continuous Fluid Bed Dryer.

Vessel 10 is operated about half full. A 20% aqueous sucralose solution feed stream is introduced intermittently into the recirculation loop ahead of heat exchanger 18, at a temperature of about 100° F., and the heat exchanger is set to heat the recirculation stream by 2° F. The vessel contents are maintained at a temperature of about 100° F., with regulation being effected by balancing heat input by the heat exchanger with evaporative cooling by flash evaporation of water, the latter being controlled by adjusting the pressure in the headspace of the vessel to about 1.0 psi absolute.

Rates of flow of the feed stream, in combination with the rate of removal of water, moist sucralose crystals and mother liquor from the process, are controlled to give a residence time of sucralose in the crystallizer vessel of about 24 hours. Crystals are collected intermittently by the centrifuge, and are dried using the above-described Procedyne dryer at a dryer temperature of about 60° F. to give a final product having a moisture content of about 0.5 wt. %.

Particle size analysis of the product is performed using a Coulter LS100Q Particle Size Analyzer, available from Coulter Corporation of Miami, Fla. The analyzer operates by light scattering, using Isopar™ G isoparaffin fluid, available from ExxonMobil Chemical of Houston, Tex., as the dispersing medium. The sucralose product crystals have a particle size distribution such that 90 wt. % of the sample has a particle size less than 62 μm, while 10 wt. % has a particle size less than from about 4 μm, with a mean of 30 μm.

The stability of this product in the previously described accelerated aging test is at least 3 days, which corresponds to about 8 years of shelf life under typical ambient storage conditions.

Although the invention is illustrated and described herein with reference to specific embodiments, the invention is not intended to be limited to the details shown. Rather, various modifications may be made in the details within the scope and range of equivalents of the claims and without departing from the true spirit and scope of the invention.

What is claimed:

1. A method of producing stable sucralose crystals from a sucralose solution, the method comprising:
   introducing a feed stream of sucralose solution into a system comprising a crystallization vessel, a heat exchanger, and a pump configured to recirculate the sucralose solution out of and back into the crystallizer vessel and through the heat exchanger;
   causing sucralose crystals to form continuously in the system;
   removing an output stream of sucralose solution including sucralose crystals from the system; and
   continuously recirculating a part of the output stream including sucralose crystals to the crystallization vessel, and separating sucralose crystals from the remaining part of the output stream;
   wherein the rates of introducing, removing, and recirculating are controlled so that sucralose passing through the system has, on average, a residence time in the system of at least four hours; and
   drying the separated sucralose crystals at a drying temperature of about 85° F. or below.

2. The method of claim 1 wherein at least one of the steps of introducing, recirculating, and removing is performed fully continuously.

3. The method of claim 1 wherein at least one of the steps of introducing and removing is performed intermittently.

4. The method of claim 1 wherein the step of introducing includes introducing at least one of the feed stream and the recirculated part of the output stream into the contents of the system tangentially to produce a swirling motion in the contents.

5. The method of claim 1 further comprising combining the feed stream and the recirculated part of the output stream prior to the step of introducing.

6. The method of claim 1 wherein the residence time is from about 6 hours to about 50 hours.

7. The method of claim 1 wherein the residence time is from about 12 hours to about 24 hours.

8. The method of claim 1 wherein the step of removing the output stream is performed at a rate to provide a turnover time of liquid in the system of from about 2 minutes to about 15 minutes.

9. The method of claim 1 wherein the step of removing the output stream is performed at a rate to provide a turnover time of liquid in the system of from about 4 minutes to about 8 minutes.

10. The method of claim 1 wherein the recirculating comprises subjecting the sucralose crystals to sufficient mechanical disturbance to fracture at least a portion thereof.

11. The method of claim 1 wherein sucralose crystals are caused to form by one or both of removing water from the system and cooling the system.

12. The method of claim 1 wherein the step of causing sucralose crystals to form continuously in the system comprises exposing the sucralose solution in the system to a pressure and a temperature sufficient to vaporize a portion of the water in the system, the method further comprising removing the vaporized water from the system.

13. The method of claim 12 wherein the pressure is between about 0.7 psi and 1.2 psi, and the temperature is between about 75° F. and about 110° F.

14. The method of claim 1 wherein the step of causing sucralose crystals to form continuously in the system comprises cooling the liquid in the system.

15. The method of claim 1 wherein the step of drying the sucralose crystals is performed at a temperature between about 50° F. and about 70° F., and the separated crystals have a moisture content of from about 0.2 wt. % to about 10 wt. %.

16. The method of claim 1 further comprising, after the step of separating sucralose crystals, drying the crystals at a temperature of about 60° F.

* * * * *